(12) United States Patent
Ryba

(10) Patent No.: US 6,991,630 B2
(45) Date of Patent: Jan. 31, 2006

(54) NON-CHARGING PRE-COOLING SYSTEM

(75) Inventor: Eric Ryba, San Diego, CA (US)

(73) Assignee: CryoCor, Inc., San Diego, CA (US)

( * ) Notice: Subject to any disclaimer, the term of this patent is extended or adjusted under 35 U.S.C. 154(b) by 158 days.

(21) Appl. No.: 10/062,678

(22) Filed: Feb. 1, 2002

(65) Prior Publication Data

US 2003/0149428 A1 Aug. 7, 2003

(51) Int. Cl.
*A61B 18/02* (2006.01)

(52) U.S. Cl. .......................................... 606/20; 606/23
(58) Field of Classification Search .............. 606/20–26
See application file for complete search history.

(56) References Cited

U.S. PATENT DOCUMENTS

| | | | | |
|---|---|---|---|---|
| 6,035,657 | A | * 3/2000 | Dobak, III et al. | ........... 62/293 |
| 6,383,180 | B1 | * 5/2002 | Lalonde et al. | ................ 606/22 |
| 6,471,694 | B1 | * 10/2002 | Kudaravalli et al. | .......... 606/21 |
| 6,497,703 | B1 | * 12/2002 | Korteling et al. | ............. 606/23 |

* cited by examiner

*Primary Examiner*—Michael Peffley
*Assistant Examiner*—Aaron Roane
(74) *Attorney, Agent, or Firm*—Fay Kaplun & Marcin, LLP

(57) ABSTRACT

A method of cooling an operative surface of a cryoablation device, comprises the steps of providing a primary refrigerant under pressure and pre-cooling the primary refrigerant to a temperature below a critical temperature thereof using a non-charging refrigeration system to liquify the refrigerant in combination with the steps of expanding the pre-cooled primary refrigerant in proximity to an operative surface of the cryoablation device and removing the expanded primary refrigerant from the proximity of the operative surface.

An apparatus for cooling an operative surface of a cryoablation device, comprises a primary refrigeration system supplying primary refrigerant to the device, the primary refrigeration system including an expansion chamber adjacent to an operative surface of the device, the primary refrigerant being expanded into the expansion chamber to cool the operative surface and a second refrigeration system to pre-cool the primary refrigerant before it reaches the expansion device, the second refrigeration system being a non-charging refrigeration system in combination with a heat exchanger coupling the primary and second refrigeration systems to one another in a heat exchange relationship.

12 Claims, 3 Drawing Sheets

NON-CHARGING PRE-COOLING SYSTEM

FIELD OF THE INVENTION

The present invention is in the field of devices for cooling biological tissues during treatment of medical conditions.

BACKGROUND INFORMATION

Cryosurgery has received increased attention as an alternative to conventional surgical techniques. Instead of using a blade to cut tissues, a surgical device with a cold tip or surface is used to cool the affected tissue to a sufficiently low temperature to ablate the tissue. For example, cryosurgical ablation is often performed to correct arrhythmia, irregular heart beat, by ablating specific regions of the heart or of veins entering the heart from which erroneous contraction impulses originate. Cryosurgery is also used extensively in dermatology, to remove abnormal tissue with less scarring than is possible using conventional surgery. Since application of a cold surface to tissues deadens the nerve endings where the tissue is removed, cryosurgery results in less pain and faster patient recovery.

Devices for performing cryosurgery vary in shape and method of use. In the case of cardiac tissue ablation, a catheter is typically introduced through the vascular system to a precise location of tissue to be treated. The tip of the catheter is then cooled to a temperature sufficiently low to ablate the tissue. These devices must be capable of cooling the operative surface to a temperature sufficiently low so that the tissue placed in contact with that surface will freeze and be destroyed. However, the diseased or degenerated tissue that must be destroyed is generally in close proximity to non-targeted, healthy tissue that should be preserved. This places complex demands on the shape, flexibility and guidance of the probe or catheter used for cryoablation, since it must be able to reach the affected area, and apply the cold selectively to the selected portion of tissue without injuring any other tissue which may be in contact with or proximity to the rest of the device.

Additional difficulties exist when the cryoablation surface is at the distal end of a catheter that is introduced into a patient's blood vessels. To avoid damaging the non-targeted tissues, the catheter cannot be cooled before the tip has reached the target tissue. Once the tip has reached the target tissue, the cooling arrangement must lower the temperature of the operative surface(s) of the tip rapidly, and must maintain the lowered temperature despite heating loads applied to the device until the desired tissue has been ablated. For example, cooling must overcome the warming effect on the catheter and the target tissue of the flow of blood through vessels in which the catheter is located. Rapid cooling of the device is complicated by the fact that the cooling surfaces may be placed a significant distance from the point at which the catheter enters the patients body. In addition, only a small portion of the device must be cooled, while the remainder must remain at a substantially higher temperature than the tip to avoid damaging non-targeted tissue.

SUMMARY OF THE INVENTION

The present invention is directed to a method of cooling an operative surface of a cryoablation device, comprising the steps of providing a primary refrigerant under pressure and pre-cooling the primary refrigerant to a temperature below a critical temperature thereof using a non-charging refrigeration system to liquify the primary refrigerant in combination with the steps of expanding the pre-cooled primary refrigerant in proximity to an operative surface of the cryoablation device and removing the expanded primary refrigerant from the proximity of the operative surface.

The present invention is further directed to an apparatus for cooling an operative surface of a cryoablation device, comprising a primary refrigeration system supplying primary refrigerant to the device, the primary refrigeration system including an expansion chamber adjacent to an operative surface of the device, the primary refrigerant being expanded into the expansion chamber to cool the operative surface and a second refrigeration system to pre-cool the primary refrigerant before it reaches the expansion device, the second refrigeration system being a non-charging refrigeration system in combination with a heat exchanger coupling the primary and second refrigeration systems to one another in a heat exchange relationship.

DETAILED DESCRIPTION

Figure 1:
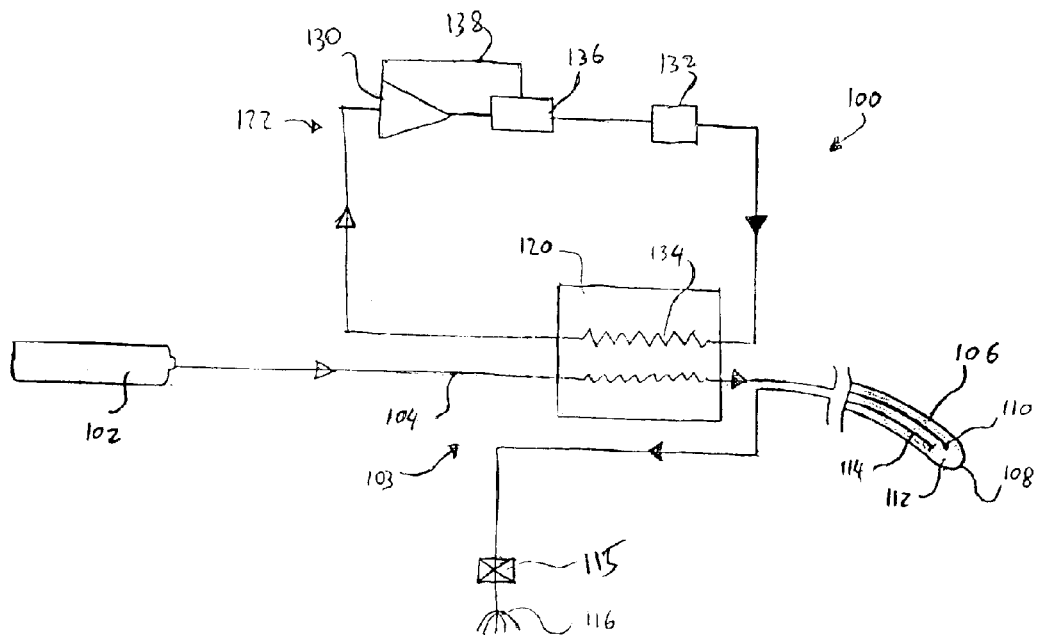
FIG. 1 is a schematic view showing a conventional pre-cooling apparatus for a cryosurgery device.

The present invention may be further understood with reference to the following description and the appended drawings, wherein like elements are referred to with the same reference numerals.

The refrigeration system used to cool the operative surfaces of a cryosurgery device must rapidly cool those surfaces and maintain them at a desired low temperature despite heating loads applied by the surrounding tissue and fluids in which the device operates. One way of achieving this result is to provide a refrigeration fluid at high pressure to an expansion chamber adjacent to the operative surface, and expand the fluid in the expansion chamber to lower the temperature of the operative surface. The fluid may, for example, be one of various refrigerant gases such as R-23, R-116 or SUVA 95. The refrigerant may also be a gas not used exclusively as a refrigerant, such as Nitrous Oxide ($NO_2$), Ethilene ($C_2H_2$), Xenon or Methane. Those skilled in the art will understand that the selection of working gas is based on the price, toxicity and thermodynamic properties of the gases.

The apparatus required to provide the refrigerant fluid to the operative surfaces of the cryoablation device may include several components. A source of pressurized fluid is connected to the proximal end of the device by conventional tubing and is connected to the distal end of the device by at least a capillary tube, which may open through an orifice into an expansion chamber located adjacent to the operative surface, usually near the distal tip of the device. In the case of a cardiac catheter, the capillary tube will have sufficient length and flexibility to be guided through blood vessels to the target tissue. A return tube is used to remove the expanded fluid from the expansion chamber, and to either vent the fluid to the atmosphere, or return it to the system for re-use. The refrigerant loop used to cool the device may be open or closed. In an open loop the refrigerant fluid is supplied under pressure, for example form a tank, and is vented after use. In a closed loop system, the refrigerant fluid is re-used, and the loop includes a device (e.g., a compressor) to bring the fluid back to the desired pressure.

The efficacy of the cooling system depends on the properties of the refrigerant fluid reaching the expansion chamber. Specifically, the difference in enthalpy of the refrigerant across the expansion orifice and the mass flow rate of the refrigerant determines in part the amount of cooling that may be applied to the operative surface, and consequently to the tissue being treated. As the mass flow of refrigerant into the expansion chamber increases, so does the amount of heat that can be removed from the tissue adjacent to the distal tip in a given time period. Similarly, a large enthalpy change during expansion of the fluid corresponds to a large temperature drop, which also results in rapid cooling of the tissue.

One way to increase the mass flow rate of refrigerant for a given capillary tube and orifice size is to cool the refrigerant being fed into the capillary tube so that its density is at a maximum value. Under normal conditions, the maximum density of a fluid is obtained when the fluid is a liquid. The refrigerant which may be provided, for example, from a tank in gaseous form, should therefore be cooled to at least its critical temperature, to turn it into a liquid. A significant improvement is obtained by this transformation from gas to liquid because of the large increase in enthalpy associated with the transition of a fluid from liquid to gas. If the refrigerant is provided to the expansion orifice in liquid form, and is expanded into the expansion chamber into a gaseous form, a large enthalpy difference may be obtained which further increases the temperature drop at the operative surface of the device.

One method to cool the refrigerant fluid below its critical temperature is to utilize a pre-cooler. The pre-cooler may be part of the refrigerant supply device, or may be a separate unit through which are routed the refrigerant tubes connecting the refrigerant supply to the cryoablation device. FIG. 1 shows schematically a conventional pre-cooling system 100, in which a refrigerant flows from a source 102 to a cryosurgery device 106 through a primary fluid line 104. The source 102 may be, for example, a compressed gas bottle, Primary line 104 may be a suitably sized tube or pipe which may terminate as a capillary tube within device 106. In one example, the device 106 may be a cryoablation catheter, with a tip 108 adapted to cool down and freeze a target region of tissue after being introduced thereto through a body lumen of a patient, via, for example, a capillary tube 110 opening into an expansion chamber 112. The expanded fluid is then removed from the expansion chamber 112 via an exhaust line 114 extending through an outlet valve 115 to an outlet 116.

The apparatus shown in FIG. 1 includes a secondary refrigerant loop 122 designed to pre-cool the refrigerant in the primary loop 103 before it is routed to the device 106. The secondary loop 122 may be a conventional refrigeration cycle including a compressor 130 to increase the pressure of the secondary refrigerant, a condenser 132 to ensure that the secondary refrigerant is in the liquid phase, and a heat exchanger section 134 in a heat exchange relationship with the primary fluid line 104 in the heat exchanger 120. This type of refrigeration cycle, requires significant lubrication of the compressor, which may result in a large quantity of lubricant being introduced into refrigerant flowing through the secondary loop 122. An oil separator used to remove some of this lubricant from the refrigerant stream, and return it to the compressor 130 via a return line 138. However, it is difficult to completely remove the oil from the refrigerant.

In certain applications may be beneficial to miniaturize the secondary pre-cooling refrigeration apparatus, so that it may be placed near the point of use of the primary refrigeration system. For example, for cardiac cryoablation, a relatively long catheter with a cooled distal tip is used by the surgeon. The distal tip is cooled by a primary refrigeration system, and it is beneficial to pre-cool the primary refrigeration fluid with a secondary refrigeration system at a location as close as possible to the point at which the catheter is connected to the primary system. This reduces the length of the connections between the catheter and the refrigeration system through which the cooled primary refrigerant must travel. This reduces the exposure of the connections carrying cooled primary refrigerant to the operating room's warmer atmosphere thereby reducing losses due to heating of the connections.

For example, the apparatus to carry out pre-cooling of the primary refrigeration system may be mounted on a movable arm placed as desired by the surgeon over the operating area. In this case, the secondary refrigeration system must be miniaturized, to fit on the movable arm. Conventional refrigeration cycles are not well suited for miniaturization, because the smaller tubes and passages can easily be clogged by oil or other contaminants that are always present in these refrigeration systems. One solution to this problem is to pre-cool the primary refrigerant utilizing a secondary refrigeration system that has no moving parts, to prevent contamination from lubricants or other matter that is a byproduct of the moving parts of conventional systems.

Figure 2:
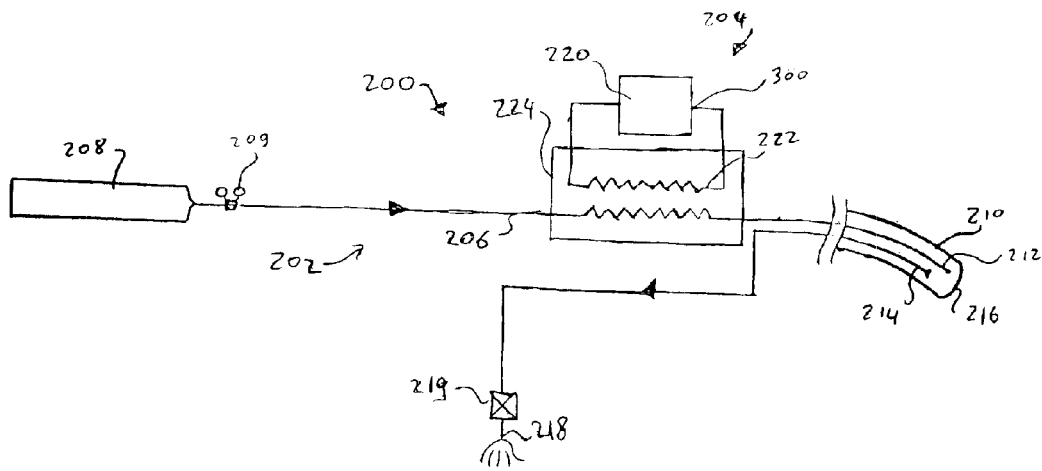
FIG. 2 is a schematic view showing an embodiment according to the present invention of a pre-cooling apparatus for a cryosurgery device.

FIG. 2 shows an exemplary embodiment of a two stage refrigeration system according to the present invention, in which the primary refrigeration fluid is pre-cooled by a secondary refrigeration system. The secondary refrigeration system is a non-charging refrigeration system, meaning that it does not have a compressor or similar device that compresses the refrigerant. As this system includes a minimum of moving parts it is suitable for miniaturization and includes no components which are susceptible to clogging due to contaminants, etc. As shown in FIG. 2, the cooling system 200 includes a primary refrigeration system 202 and a secondary refrigeration system 204 used to pre-cool the refrigerant in the primary system 202. The refrigerant fluid may, in one embodiment, be supplied to the primary system 202 by a supply bottle 208 coupled to a pressure regulator 209.

In one exemplary embodiment, the refrigerant of the primary system may be Nitrous Oxide ($NO_2$), however other fluids may be selected based on their thermodynamic properties. Principally, the evaporation and condensation temperatures and pressures of the gases, as well as their change in enthalpy when changing phase are important in selecting a refrigerant fluid that produces the required low temperatures and cooling capacity, while remaining within acceptable pressure limits. In this exemplary embodiment, the $NO_2$ may be at a pressure of about 400 PSI before being expanded to atmospheric pressure in the expansion chamber of the catheter 210. Other gases may be used according to the invention, such as SUVA 95 and $C_2H_2$. Although $C_2H_4$ and Methane may also give good results, these are less desirable as they are flammable. Xenon also gives good results, but is more costly that the previously listed refrigerants.

The refrigerant travels through the tube 206 from the bottle 208 to a capillary tube 212 within the catheter 210. The refrigerant is expanded in an expansion chamber at the distal end of the catheter 210 and cools the distal tip 216 thereof. Those skilled in the art will understand that expansion may be achieved using an orifice, a throttling valve, or any other conventional expansion device. After expansion, the now gaseous refrigerant may be withdrawn from the body through a return lumen 214 in the catheter 210 and vented to the atmosphere via a venting outlet 218. Alternatively, the return lumen 214 may return the refrigerant to the system for re-use. A flow control valve 219 may be included in the primary refrigeration system 202 to control the flow rate of the refrigerant therethrough. The expanded refrigerant may be used again in the primary refrigeration cycle. However contaminants may be contained in the re-used refrigerant which, if not removed, may clog the narrow capillary tube 212 and the return lumen 214 within the catheter 210.

When the primary refrigerant leaves the bottle 208 it is in gaseous form, and remains gaseous until it passes through a pre-cooler heat exchanger 224. A secondary refrigeration system 204 is used in the pre-cooler heat exchanger 224 to cool the primary refrigerant and to condense it to a liquid. The liquefied primary refrigerant is then expanded in the catheter 210 as described above, to produce much greater cooling than would be possible without pre-cooling of the refrigerant. In one exemplary embodiment, the expansion of pre-cooled $NO_2$ may achieve and maintain a temperature of the tip 216 of about –80C to –90C. This low temperature is suitable for cardiac cryoablation applications. For other applications compatible with higher ablation temperatures, (e.g., dermatology), the present exemplary system may be operated at a reduced cooling capacity, to achieve the desired temperatures.

Figure 3:
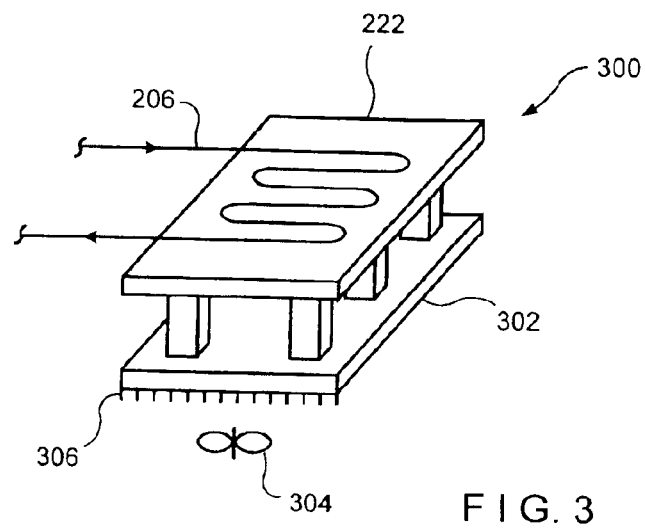
FIG. 3 is a schematic view showing a detail of the embodiment depicted in FIG. 2.

As shown in FIGS. 2 and 3, the non-charging secondary refrigeration system 204 may include, for example, a Thermo-Electric (TE) or Peltier cooler 300. The TE cooler 300 is used to pre-cool the primary refrigerant in the conduits 206 before it reaches the catheter 210. In this example, the TE cooler 300 is a solid state device. As would be understood by those of skill in the art, the TE cooler 300 includes a cold plate 222 and a hot plate 302. Supplying an appropriate voltage and current from a power supply 220 to the TE cooler 300, lowers the temperature of the cold plate 222 while the temperature of the temperature of the hot plate 302 is raised. As shown in FIG. 3, the conduit 206 may be placed in a heat exchange relationship with the cold plate 222, so that the primary refrigerant flowing therethrough is pre-cooled, Those skilled in the art will understand that the materials forming the portion of the conduit 206 which adjacent to the TE cooler 300 should be selected to maximize the heat exchange with the cold plate 222. Examples of suitable materials include known heat conducting alloys. The amount of cooling provided by TE cooler 300 is a function of the flow rate and initial temperature of the primary refrigerant, and of the heat transfer with conduits 206. The primary requirement of TE cooler 300 is to cool the primary refrigerant below its critical temperature, thus condensing it into the liquid phase. For example, the TE cooler 300 may include one or more units of about 50 Watts power, capable of cooling the cold plate 222 to about –40 C. Those skilled in the art will understand that applying current to a Peltier cooler creates a temperature difference between the hot and cold plates thereof. Thus, increasing amounts of cooling may be obtained by stacking individual Peltier coolers on top of one another with the hot plate of one cooler contacting the cooling plate of another until the desired temperature is obtained on the final Peltier cooler.

The heat may be dissipated from the hot plate 302 of the TE cooler 300 by, for example, cooling fins 306 and/or by suitably locating the TE cooler 300 in a location where natural convection will achieve the necessary cooling of the hot plate 302. Alternatively, a fan 304 or other method of forcing cooling air over the hot plate 302 may be used. In a further alternative embodiment, a liquid cooling system may be used to remove heat from the hot plate 302, for example by way of a radiator circulating cooling water over or through the hot plate 302.

Figure 4:
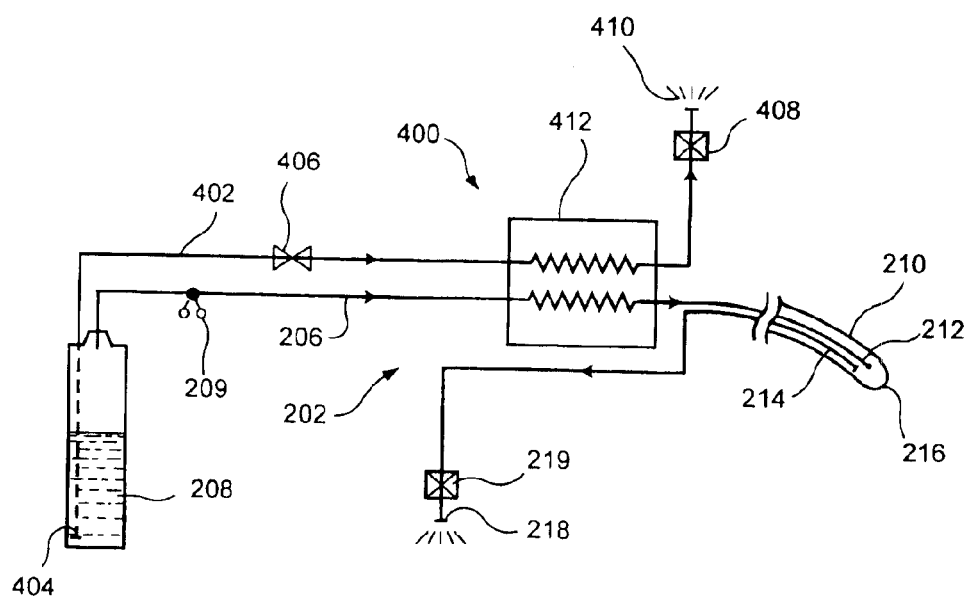
FIG. 4 is a schematic view showing another embodiment according to the present invention of a pre-cooling apparatus for a cryosurgery device.

FIG. 4 shows another exemplary embodiment of a cooling system according to the present invention. The primary refrigeration system 202 of this embodiment is similar to the primary system described with reference to FIG. 2 with a conduit 206 carrying the primary refrigerant from a storage bottle 208 to a capillary tube 212 in the catheter 210. The refrigerant is expanded into an expansion chamber in the cooling tip 216 to cool the tip 216 before it is removed via a return lumen 214. In this exemplary embodiment, pre-cooling of the primary refrigerant is accomplished in a pre-cooling heat exchanger 412, in which the primary refrigeration system 202 is placed in a heat exchange relationship with a non-charging secondary refrigeration system 400.

The secondary refrigeration system 400 of this exemplary embodiment includes a liquid extraction tube 404 which reaches into the bottom of storage bottle 208, where the refrigerant is stored in liquid form as a result of gravity. This is in contrast with the conduit 206, which retrieves gaseous refrigerant from the top of the bottle 208. In this exemplary embodiment the refrigerant contained in the bottle 208 may be $NO_2$. However, those skilled in the art will understand that other refrigerant fluids may be used, so long as their thermodynamic properties match the requirements of the primary and secondary refrigeration systems 202, 400, as discussed above. In an alternative embodiment, the primary and secondary refrigerants may be different fluids. However, the embodiment described in detail herein uses the same fluid for both the primary and secondary refrigeration systems, 202, 400, respectively.

The secondary refrigerant exits the bottle 208 at a pressure between about 700 and 800 PSI. In this exemplary embodiment, the secondary refrigerant is in liquid form and its pressure is not reduced via a pressure regulator. The secondary refrigeration system 400 may include an expansion valve 406 to selectively expand the secondary refrigerant fluid, and reduce its temperature as it vaporizes. In one embodiment, the secondary refrigeration system 400 is open to the atmosphere at a vent 410, and a valve 408 is used to control the flow rate of the secondary refrigerant. The expanded secondary refrigerant is introduced into a pre-cooler 412, where it is placed in a heat exchange relationship with the refrigerant in the primary system 202. As a result, the primary refrigerant is cooled below its critical point, and condenses to a liquid. Neither the pre-cooler heat exchanger 412 nor the entire secondary refrigeration system 400 has any moving parts that may generate contaminants, and thus may be miniaturized with minimum reliability concerns due to blocked passages, etc.

Figure 5:
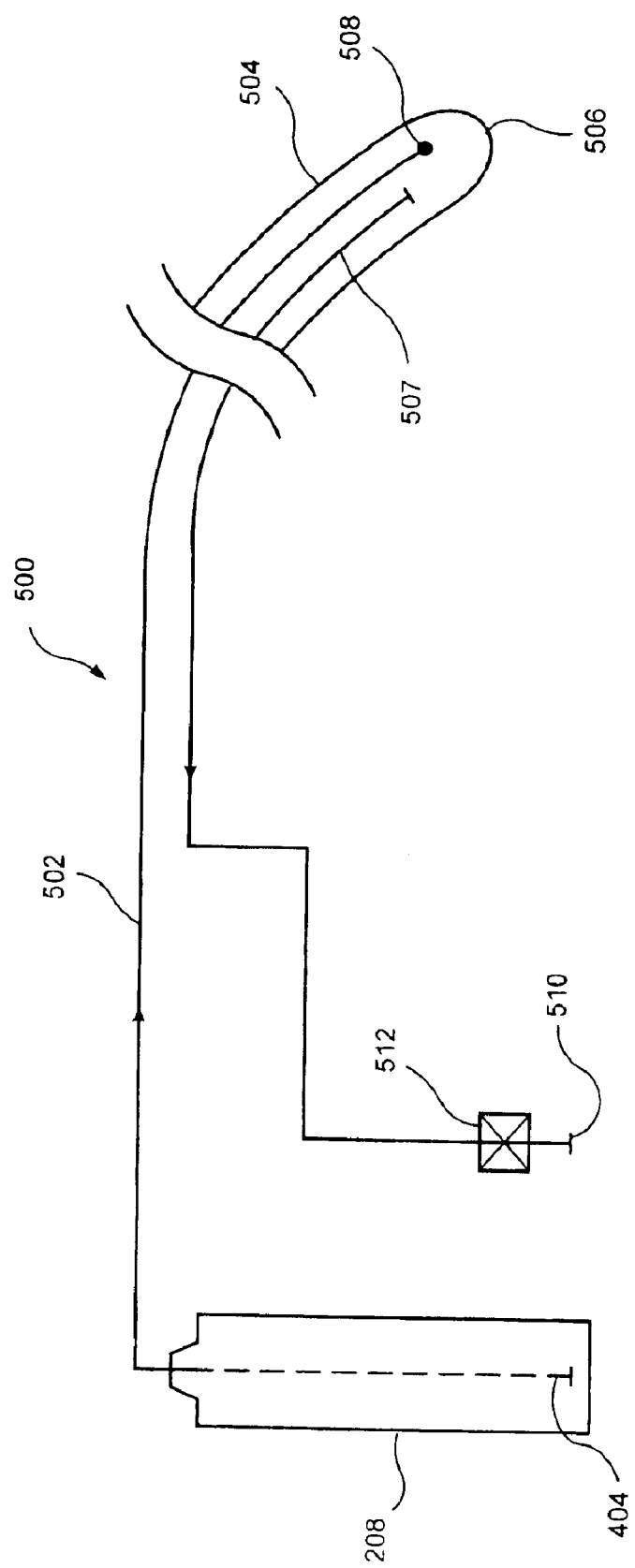
FIG. 5 is a schematic view showing a third embodiment according to the present invention of a pre-cooling apparatus for a cryosurgery device.

FIG. 5 shows a further exemplary embodiment of a refrigeration system according to the present invention. In this embodiment, the refrigerant fluid in the primary refrigeration system 500 is not pre-cooled by a secondary refrigeration system. The primary refrigerant is removed from the storage bottle 208 via a liquid extraction tube 404, so that the primary refrigerant is already in the liquid phase. The liquid refrigerant is carried by the tube 502 to the catheter 504, where it reaches an orifice 508, and is expanded to produce the desired cooling of a tip 506. A return tube 507 may be vented to the atmosphere via a vent 510 and a flow rate control valve 512 as described more fully above.

According to the exemplary embodiment shown in FIG. 5, the refrigerant fluid may be $NO_2$, so that the desired temperature drop and cooling power may be achieved as described above. For example, the pressure of the $NO_2$ before expanding through the orifice 508 may preferably be between approximately 800 and 900 PSI, so that the primary refrigerant remains in the liquid phase without additional cooling. As indicated above, other gases with appropriate thermodynamic properties may be used instead of $NO_2$, depending in part on the desired temperatures to be achieved on the operative surfaces of tip 506.

In the preceding specification, the present invention has been described with reference to specific exemplary embodiments thereof. It will, however, be evident that various modification and changes may be made thereto without departing from the broadest spirit and scope of the present invention as set forth in the claims that follow. The specification and drawing are accordingly to be regarded in an illustrative rather than restrictive sense.

What is claimed is:

1. A method of cooling an operative surface of a cryoablation device comprising:

obtaining a primary refrigerant in a gaseous phase from a source;

providing the primary refrigerant under pressure to a primary refrigeration system;

obtaining a second refrigerant in a liquid phase from the source;

pre-cooling the primary refrigerant to a temperature below a critical temperature thereof using the secondary refrigerant in a non-charging refrigeration system to liquify the primary refrigerant;

expanding the pre-cooled primary refrigerant in proximity to an operative surface of the cryoablation device; and removing the expanded primary refrigerant from the proximity of the operative surface.

2. The method according to claim 1, wherein the pre-cooling step further comprises expanding the second refrigerant in the non-charging refrigeration system, and placing the non-charging refrigeration system in a heat exchange relationship with the primary refrigerant.

3. The method according to claim 1, further comprising reducing a pressure of the primary refrigerant to between approximately 300 and 400 PSI prior to the expansion step.

4. The method according to claim 1, wherein the non-charging refrigeration system expands the second refrigerant to pre-cool the primary refrigerant.

5. An apparatus for cooling an operative surface of a cryoablation device, comprising:

a source of refrigerant;

a primary refrigeration system supplying primary refrigerant received in gaseous phase from the source to the device, the primary refrigeration system including an expansion chamber adjacent to an operative surface of the device, the primary refrigerant being expanded into the expansion chamber to cool the operative surface;

a second refrigeration system receiving second refrigerant from the source in liquid phase and expanding the secondary refrigerant to pre-cool the primary refrigerant to supply the primary refrigerant to the expansion chamber in the liquid phase, the second refrigeration system being a non-charging refrigeration system; and a heat exchanger coupling the primary and second refrigeration systems to one another in a heat exchange relationship.

6. The apparatus according to claim 5, wherein the second refrigeration system further comprises a heat exchanger to place the expanded second refrigerant in a heat exchange relationship with the primary refrigerant.

7. The apparatus according to claim 6, where the refrigerant source includes a storage bottle.

8. The apparatus according to claim 6, wherein the second refrigerant is one of $NO2$, $C2 H2$ and SUVA 95.

9. The apparatus according to claim 6, further comprising a valve to control a flow rate of the second refrigerant through the second refrigeration system.

10. The apparatus according to claim 5, wherein the primary refrigerant is one of $NO2$, $C2 H2$ and SUVA 95.

11. The apparatus according to claim 5, wherein the operative surface is cooled to a temperature of between −80° C. and −90° C.

12. The apparatus according to claim 5, wherein the second refrigeration system cools to a temperature of about −40° C.

* * * * *